United States Patent [19]

Seaver

[11] Patent Number: 4,699,511
[45] Date of Patent: Oct. 13, 1987

[54] REFRACTION SENSOR

[76] Inventor: George A. Seaver, Box 401, Cataumet, Mass. 02534

[21] Appl. No.: 719,399

[22] Filed: Apr. 3, 1985

[51] Int. Cl.$^4$ ............................................. G01N 21/41
[52] U.S. Cl. ..................................... 356/136; 356/135
[58] Field of Search ............... 356/136, 137, 135, 133, 356/128

[56] References Cited

U.S. PATENT DOCUMENTS 4,306,805 12/1981 Arrington ........................... 356/133
4,372,165 2/1983 Pitt et al. ............................ 356/133
4,427,293 1/1984 Harmer ............................... 356/136

FOREIGN PATENT DOCUMENTS 0020889 2/1977 Japan ................................... 356/133

OTHER PUBLICATIONS

"Variable Angle Reflection Attachment for the Ultraviolet, Visible, and Infrared", Hansen, *Analytical Chemistry*, vol. 37, #9, pp. 1142-1145, 8/1965.
"A Method of Measurement of the Pitch and Refractive Indices of Cholestric Liquid Crystals Using Selective Reflections and Total Reflections", Tako et al., *Japanese Journal of Applied Physics*, vol. 14-1, pp. 425-428, 1975.

*Primary Examiner*—R. A. Rosenberger
*Assistant Examiner*—Crystal D. Cooper
*Attorney, Agent, or Firm*—Norman S. Blodgett; Gerry A. Blodgett

[57] ABSTRACT

An index of refraction sensor utilizing a sensor face inclined at the nominal critical angle of an incident beam, refracts or reflects this incident radiation depending upon the wavelength of that radiation and the index of refraction external to it. The refraction sensor apparatus includes a broadband radiant energy source, a radiant energy guidance and collimating means, a prism sensing element interposed in the radiant energy guide, and a detector for continuously detecting the spectral intensities of the broadband radiant energy reflected by the prism sensing element. Advantageously, a single mode optical fiber may be used as the radiant energy guidance and collimating means for directing the broadband radiant energy to the prism and a multimode optical fiber may be used for returning the reflected radiant energy to the detector. The prism sensing element is fabricated of a suitable transparent material, that material ranging from silica to dense flint glass to titanium dioxide depending upon the desired optical dispersion and sensitivity. Additionally, the single mode optical fiber end itself can be ground and polished to be the prism sensing element and, with a mirrored face at a particular angle to the reflected ray, the single mode fiber can also be the return guidance means to the detector.

11 Claims, 9 Drawing Figures

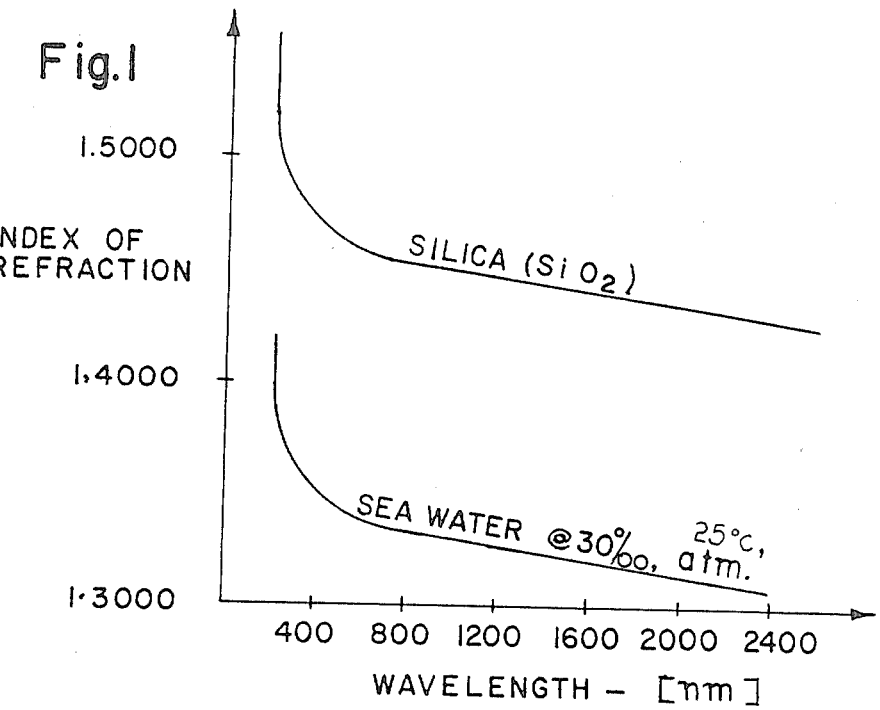
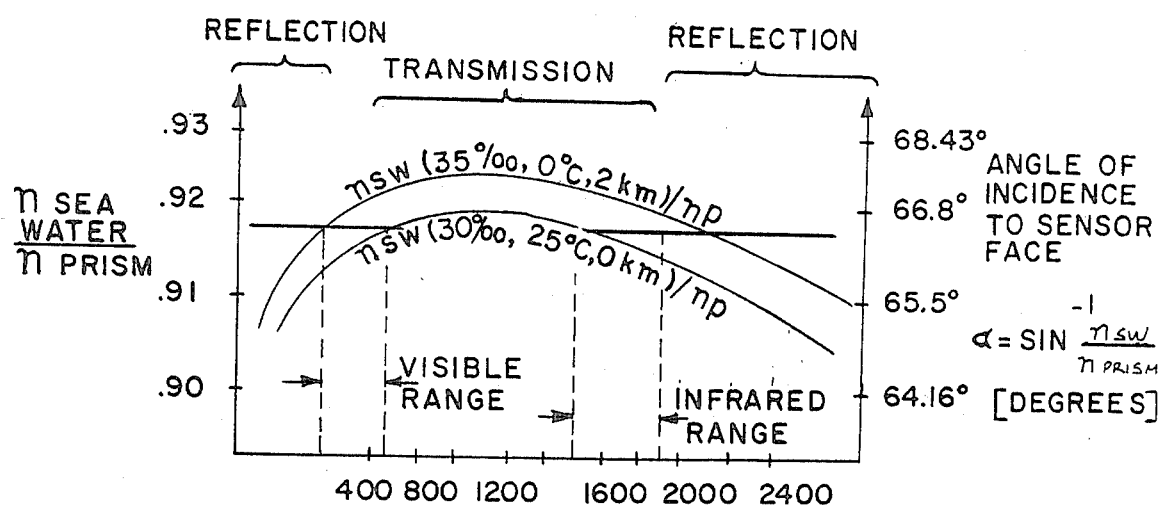
Fig.2 SiO₂ SENSOR WITH SEA WATER

REFRACTION SENSOR

BACKGROUND OF THE INVENTION

1. Field of the Invention

This invention relates to index of refraction sensors and, more particularly, to a critical angle refractometer in which the wavelength rather than the angle for critical reflection of the incident energy is continuously measured as a function of the external index of refraction.

2. The Prior Art

In conventional refractometers the variation of the critical angle for monochromatic incident radiant energy is measured as a function of the external index of refraction. Examples of these Abbe laboratory refractometers are Gaertner Scientific corporation's model No. L128-94 and American Optical's model No. 10450. An example of an in-situ Abbe refractometer utilizing an optical fiber to direct the monochromatic radiant energy to the sensor and an electrical wire to direct the voltage signal from the sensor to the detector is described in Mahrt, et. al. (1982).

Other examples of the principle of the Abbe refractometer are found in Hansen (1965) and Tako et al. (1975). These last two examples also incorporate some aspects of the critical wavelength technique as well, although their accuracy and resolution is quite limited and they do not measure continuously.

Other refractometers use broadband, non-coherent, non-collimated radiant energy and measure the intensity of the transmitted or reflected radiant energy as a function of the external index of refraction of the fluid; these refractometers can read remotely from the radiant energy source and sensor, usually through optical fiber transmission links, but have drift and calibration difficulties. Examples of this approach are found in Abuaf, et. al. (1978) in which incandescent radiant energy is guided through multimode optical fibers to a 45°-90°-45° glass prism and returned to a detector through a second multimode fiber. The radiant energy is reflected from the prism when it is in air and refracted out when it sees water; it is used to detect water in two phase flows. Another example is that of Harmer (1983) in which radiant energy from a light emitting diode is guided through a multimode optical fiber which is bent into an "S" shape in the region in which it is desird to measure the index of refraction. The radiant energy that is not refracted out in the "S" portion is returned to the detector through a straight multimode optical fiber. The detector then relates the intensity of the incident radiation to the index of refraction external to the "S" region.

Arrington (1981) and Uramoto (1977) are also examples of the above intensity-modulated refractometers in which critical reflection plays a minor role.

To be completely useful and widely accepted in such fields as oceanography, it is desirable that the refraction sensor be less than 0.6 mm in diameter, have a stable calibration with an accuracy in the index of refraction of $1 \times 10^{-5}$, be capable of reading remotely, and continuously, be inexpensive and simple with the possibility for expendable use, and be suitable for use in the oceans. Such an index of refraction sensor is disclosed and claimed herein.

REFERENCES CITED

Abbe Refractometer, 1880. (a) Gaertner Scientific Corporation, 1201 Wrightwood Ave., Chicago, Ill. 60614. Model No. L128-94. (b) American Optical, Buffalo, NY 14215. Model No. 10450.

Abuaf, N., O. C. Jones, and G. A. Zimmer, 1978. Review of Scientific Instruments, 49(8). p. 1090-1094.

Hamer, A. L., 1983. Proceedings of the First International Conference on Optical Fiber Sensors. IEE, Savoy Place, London England and Optical Society of America, Washington, D.C. Apr. 26-28, 1983.

Mahrt, K.-H., H. C. Waldmann, and W. Kroebel, 1982. Proceedings of the Oceans '82 Conference, IEEE/MTS, Washington, D.C. Sept. 20-22, 1982.

Arrington, J., 1981: "Refractometric Device". U.S. Pat. No. 4,306,805.

Uramoto, H., 1977: Device for Determination of the Refractive Index of a Fluid". Japanese Patent No. 52-20089 of Feb. 17, 1977.

Hansen, W., 1965: "Variable angle reflection attachment for the ultraviolet, visible, and infrared". Anal. Chem, 37, 9, p. 1142-1145.

Tako, T.; T. Akahane; and S. Masubuchi, 1975: "A method of measurement of the pitch and refractive indices of cholesteric liquid crystals using selective reflections and total reflections". Jap. Jnl. of Appl. Phys. 14, Suppl. 14-1, p. 425-428.

Pitt, G.; R. Williamson, 1983: "Apparatus for measuring fluid flow". U.S. Pat. No. 4,372,165 of Feb. 8, 1983.

BRIEF SUMMARY AND OBJECT OF THE INVENTION

This invention relates to an index of refraction instrument which relies upon the wavelength shift of the optical band edge reflected from a prism face as a function of the index of refraction external to that prism face. Operating with a broadband collimated ray spanning the wavelength of the reflection/refraction band edge at a prism face, a change in index on one side of the face causes the wavelength of the reflection/refraction band edge to change depending upon the dispersive characteristics of the indices on either side of the prism face. In this approach, instead of measuring the angle just at total internal reflection for a monochromatic radiant energy source, as in the Abbe refractometer, we will be measuring the wavelength at total reflection for a constant incidence angle and a white broad band radiation source, making use of the differing dispersion relations on either side of the prism sensor/external material interface. The broad-band source allows for continuous measurement of the refractive index; and the sensor is essentially a dispersing prism operated at a median critical angle with the collimation of the incident broad band radiant energy done by a single mode optical fiber and microlens by collimating slits. The wavelengths of the reflection band edge is measured by noting the wavelengths where a sudden change in spectral intensity occurs and, with the index of the prism sensor and the angle of incidence to the prism face known, the index of the external material is then determined from Snell's Law. If the index of the external material is known, such as in the case of air, then the index of the prism material can be determined.

It is, therefore, a primary object of this invention to provide an optical index of refraction sensor that is compatible with and sometimes indentical with optical fibers.

Another object of this invention is to provide improvements in remote, accurate, fine scale index of refraction sensors that measure the index continuously.

A third object of this invention is to provide an optical fiber index of refraction sensor that is expendable.

These and other objectives and features of the present invention will become more fully apparent from the following description and appended claims taken in conjunction with the accompanying drawings.

BRIEF DESCRIPTION OF THE DRAWINGS

FIG. 1 is a graphical comparison between the indices of refraction of silica ($SiO_2$) and sea water and the wavelength at which they were determined.

FIG. 2 is a graphical comparison between the ratio of the external material index of refraction and prism sensor index and the wavelength at which they are determined.

DETAILED DESCRIPTION OF THE PREFERRED EMBODIMENT

Figure 3:
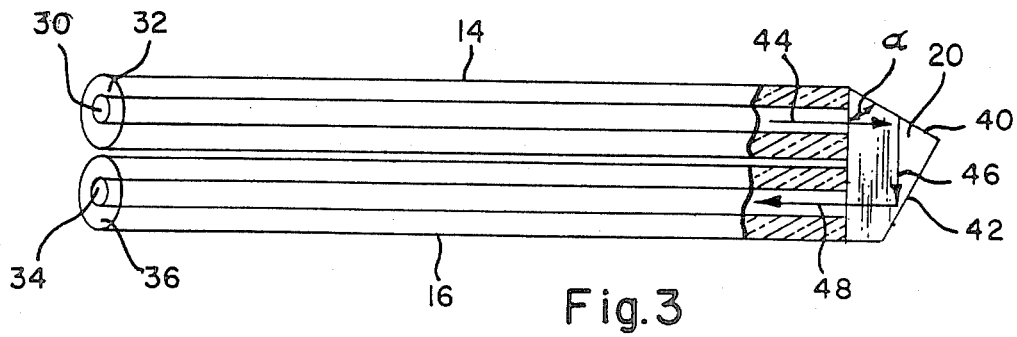
FIG. 3 is a schematic enlargement of one presently preferred embodiment of the sensor tip region of the index of refraction instrument of FIG. 5.

The invention is best understood by reference to the drawings wherein like parts are designed with like numerals throughout.

THEORY OF OPERATION

The operation of the refraction sensor proposed here is based upon two principles: the intensity of the reflection from a surface increases according to the Fresnel equations very rapidly as the critical angle is approached, and the index of refraction changes different with wavelength in transparent prisms as opposed to the external sample material. The result is that for a broadband collimated illuminating source the refraction sensor is a band pass filter whose multiple band edges are functions of the index of refraction of the external material. The multiple nature of the band edges is a direct result of the different effects in the two different materials from atomic interaction with the visible radiation and then molecular interaction with the infrared radiation. The broad band, as opposed to monochromatic, nature of the source provides for the continuous tracking of these band edges and their associated indices of refraction.

The relationship between the index of refraction of a medium and the wavelength of radiant energy in that medium is called the dispersion relation. The dispersion relation for most transparent prism materials, semiconductors, and many fluids is well known. From the equally well known Snell's law when the ratio of the index of the external material to that of the prism sensor is equal to the cosine of the angle between the radiant energy ray and the prism sensor face, the critical angle is reached and the radiant energy goes from a refracted and reflected ray to a totally reflected ray. This invention measures the wavelength at which this occurs and relates it to the external index of refraction; there are in practice two critical wavelengths for a given prism, angle of incidence, and external index:

As an illustrative example, we will consider silica ($SiO_2$), such as found in optical fibers, as the prism sensing material and sea water as the external material. The index of refraction (which is the normalized speed of light in the material) for silica and two representative sea water samples is shown in FIG. 1. As the wavelength increases from the ultraviolet, the index of refraction of silica falls off more rapidly and levels off sooner than does that of sea water, as the atomic interaction with the radiation diminishes sooner for silica than for sea water. The result is that the ratio of their indices, which is the sine of the angle required for critical reflection, first increases and then decreases. This is shown in FIG. 2 and results in two critical wavelengths and two band edges for a given angle of incidence and external sample in the regime of *atomic* interaction with the radiation (100 nm to 2400 nm). Additional critical wavelengths and band edges can frequently be found further out in the infrared, as the *molecules* of the sensing prism and external sample begin to interact with the radiation. In FIG. 2 only the spectrum and band edges associated with the atomic interaction are shown, as these are the only wavelengths that can be conveniently read with conventional scanning detectors. FIG. 2 shows that for a 66° angle between the incident beam and the normal to the sensor face, which is angle x, and for a sea water to silica index ratio of 0.918, then critical reflection occurs, and for the region of atomic influence on the radiation, this occurs at two wavelengths, one in the visible and another in the infrared. As the wavelength of the incident radiant energy increases beyond the visible critical value further into the visible or decreases from the infrared value, the reflected energy falls off rapidly as is described very precisely by the well known Fresnel Reflection equations and the dispersion relations. We then have a band rejection filter for reflection, band pass for transmission, whose band edges are very steep and are functions of the external index of refraction. These results are presented in the example of FIG. 4, where the intensity of the radiant energy reflected from the silica ($SiO_2$) prism face 40 (FIG. 3) is compared with the wavelength of that radiant energy for two different external fluids. We see that for one seawater fluid and alpha, the band edge is at 640 nanometers in the visible and at 1480 nanometers in the infrared and for a denser seawater fluid the band edge is at 400 nm in the visible and at 1900 nm in the infrared. For this application with seawater as the external fluid whose index of refraction we wish to measure, the normal to the prism sensor face 40 is at an angle of 66.8° to the incident beam. The band edge signal for the critical angle of FIGS. 2 and 4 is between 3 and 5 decibels in amplitude with 2 db occurring over 20 nm.

Figure 5:
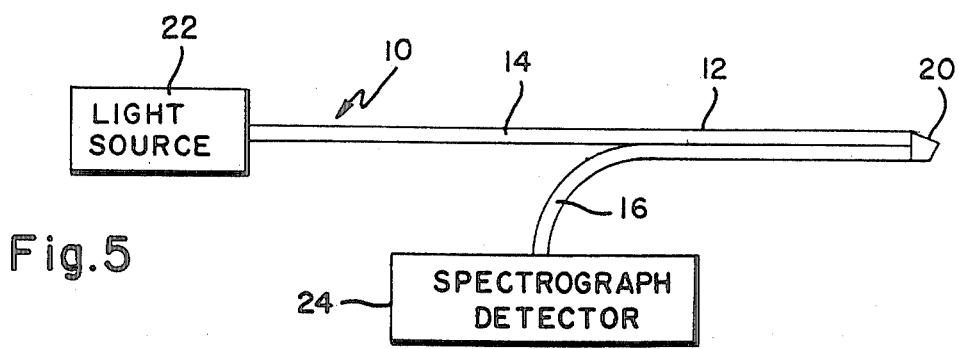
FIG. 5 is a schematic plan view of one presently preferred embodiment of the index of refraction instrument of this invention.

In operation once the wavelength of the critical angle has been developed by the light source, prism sensor, and detector of FIG. 5, the index of refraction of the external material is determined by imposing the well known Snell's Law for refraction, and in particular, for refraction at the critical angle. We then have:

Index of fluid at wavelength $\lambda c = \sin \alpha \times$ index of prism at $\lambda c$. This result is presented in the example of FIG. 6 where the index of refraction of seawater is compared with the wavelength of the critical angle for the silica prism and seawater interface. The normal to the prism sensor face makes an angle $\alpha$ of 66.8° with the incident radiant energy ray and is the critical angle.

CONSTRUCTION

Referring to FIG. 5, a schematic illustration of a first preferred embodiment of the index of refraction sensor of this invention is shown generally at 10 and includes a fiberoptic probe 12. Fiber optic probe 12 includes at least two optical fibers 14 and 16 which are each approximately 0.25 mm in diameter and are optically coupled by a specially shaped sensor 20. The shaped sensor 20 is fabricated as a prism, as will be set forth in the description of the invention concerning FIGS. 3, 7 and 8.

Optical fiber 14 is optically coupled to a broad-band white radiant energy light source 22 and serves as a conducting means for conducting the white radiant energy from source 22 to the prism sensor 20. As the angle between the radiant energy ray 44 and the prism sensing face 40 of FIG. 3 must be controlled very precisely, the ray must be highly collimated. In the first preferred embodiment, single mode optical fiber is used for the guidance means to the prism 20 with a microlens between the fiber and the prism for even better collimation. Such a fiber is Corning Glass Works SMF No. 68702 and is single mode and guiding for the wavelength range 0.4 microns to 1.3 microns, and such a microlens is Nippon Sheet Glass Selfoc lens SLN-20. Optical fiber 16 which can be multimode is optically coupled between the prism 20 and the spectrograph detector 24 of FIG. 5 and serves as a conducting means for conducting the index of refraction variable radiant energy reflected by prism 20.

The wavelength range of the radiant energy source 22 is specifically chosen, in conjunction with the prism material and face angle $\alpha$, to cover the external material's index of refraction range of interest. This would be accomplished by considering a diagram such as depicted in FIG. 2. This diagram is for a silica prism material, a sensor face angle $\alpha$ of 66.8. degrees, and two external seawater limits. One is for: 35 parts per thousand salinity, 0 degrees centigrade temperature, 3000 pounds per square inch pressure; and the second is for 30 parts per thousand salinity, 25 degrees centigrade temperature, and atmospheric pressure. For the above parameters a band width for the radiant energy source 22 of 400 nanometers to 650 nanameters in the visible and/or 1500 nm to 1900 nm in the infrared would be required. This band width of radiant energy would be met by a tungsten-halogen light source; also the above sea water limits would cover most situations met in oceanography.

Figure 4:
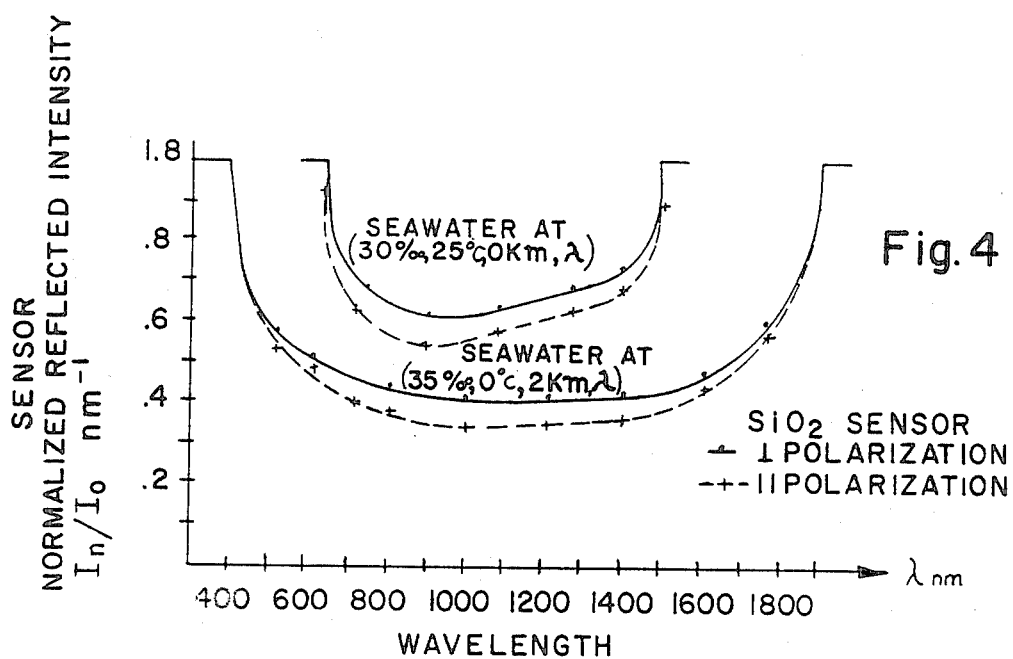
FIG. 4 is a graphical comparison between the intensity of radiant energy reflected by the prism sensor face, in this case a silica prism in seawater, and the wavelength of that radiant energy.

Referring now to FIGS. 3 and 5, the index of refraction variable radiant energy 48 reflected from the prism sensor face 40 is guided by optical fiber 16 to the spectrograph detector 24. In this detector the incident radiation 48 is spread out in an angular manner by a dispersing prism. This distribution in space of the intensity of the various wavelengths of the reflected radiant energy is imaged upon a commercially available photo detector that has individual pixels sensitive to this incident radiation. Such an element could be a charged couple device (CCD) and its output would be of the simultaneous spectral intensities of the radiation compared with the wavelength of that intensity. The CCD would then continuously display the band edge and its wavelengths. An example of such spectral intensities is shown in FIG. 4. This spectrograph detector resolves to 0.1 nanometers or better and gives the index of refraction of the external fluid to one part in $10^{-5}$ or better.

Referring again to FIG. 3, the sensing tip of the index of refraction probe 12 is shown schematically and greatly enlarged for ease of illustration. Single mode optical fiber 14 is configured with a core 30 and a cladding 32. Correspondingly, a single or multimode optical fiber 16 is configured with a core 34 and a cladding 36.

Prism sensor 20 is fabricated with a carefully ground and polished sensing face 40 and a mirrored reflecting face 42 and an incident face 43. The prism sensor 20 and, more particularly, sensor face 43 is optically coupled to the ends of optical fibers 14 and 16, and, more particularly, to cores 30 and 34 therein, respectively. In order to set precisely the prism sensor face 40 in the correct angle $\alpha$ to the incident radiation ray 44 the following method is used. White light source 22 (FIG. 5) illuminates prism sensing face 40 which is approximately ground to an angle $\alpha$ such as 64 degrees or so that all of the incident ray 44 is reflected through the face 40. This is done with the sensor face 40 immersed in a fluid of index of refraction slightly larger than the maxima it will encounter in service; sensor face 40 is then ground and polished so that it just begins to reflect violet light. Then the second prism face 42 is ground to be 90 degrees from face 40 or until, with the prism 20 now in air, it reflects ray 48 into optical fiber core 34. This second prism face 42 is then mirrored to be totally reflecting.

Figure 6:
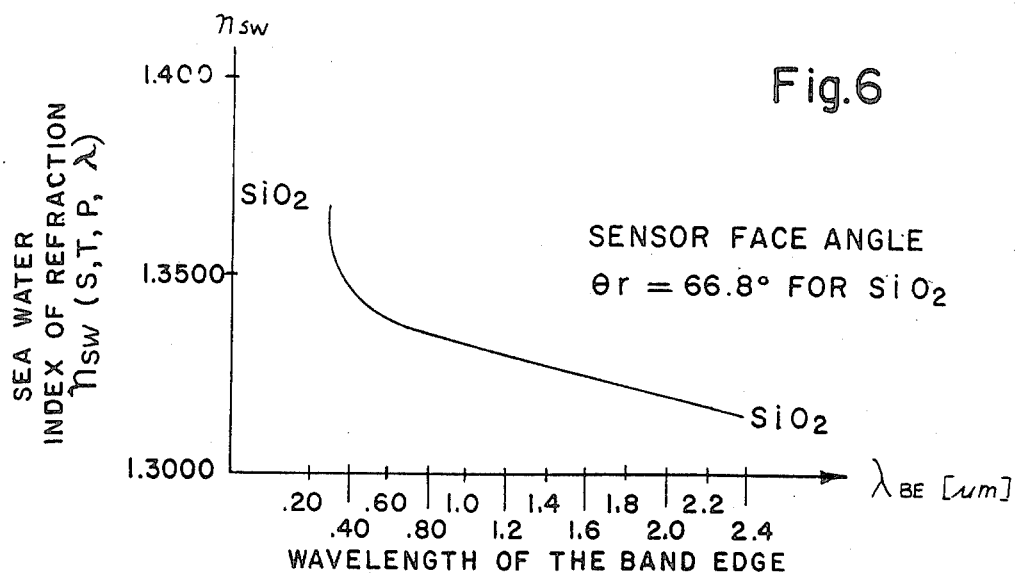
FIG. 6 is a graphical comparison between the wavelength of the band edge of the radiant energy relfected from the prism sensor face and the index of refraction of the material external to that face, in this case seawater surrounding a silica ($SiO_2$) prism sensor.

In the embodiment illustrated herein, the white light emitted by source 22 (FIG. 5) is indicated schematically as ray 44 in core 30 of optical fiber 14. Ray 44 strikes face 40 of the prismatic configuration of refraction sensor 20 and is partially reflected as ray 46 to face 42 where it is totally reflected by face 42 as ray 48. In its traversal of sensor face 40, only a certain band width of the broad-band radiant energy 22 is reflected and this reflection is a function of the index of refraction of the material external to refraction sensor 20. Accordingly, the wavelengths of the band edge of the reflected ray will become shorter or longer as the index of refraction of the material external to the prism is increased, the sign depending upon the relative dispersions of the refraction sensor 20 and the external material. The wavelength of the band edge is determined by noting the wavelength were the spectral intensity of the reflected ray 48 abruptly changes. increased. The wavelength of the band edge of the reflected ray 48 is then continuously readable with the spectograph detector 24 as the index of refraction of the material external to the refraction sensor 20, as set forth in a calibration curve, such as shown in FIG. 6. If the index of refraction and dispersion of the external material is known, such as with air, then this process will give the index of refraction of the sensor 20.

Only two optical fibers 14 and 16 are shown in FIG. 5. However, it may be found desirable to include additional optical fibers in probe 12 for the purpose of providing suitable radiant energy guide means to the detector. Furthermore, increasing the number of optical fibers from two to four would not substantially alter the effective diameter of probe 12 which is about 0.6 mm; there would be a slight increase in the diameter with a doubling of the radiant energy carrying capacity.

Figure 7:
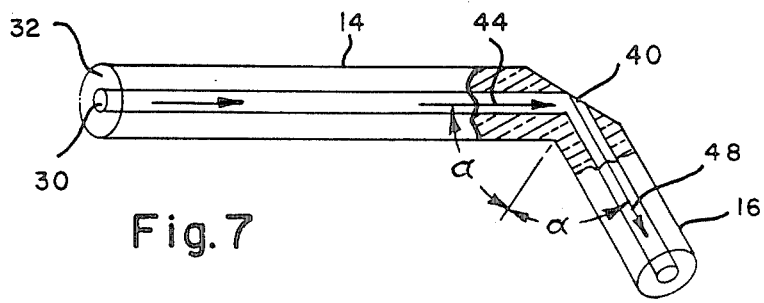
FIG. 7 is a schematic enlargement of a second preferred embodiment of the sensor tip region of the index of refraction instrument of FIG. 5.

Referring now more particularly to FIG. 7, a second configuration of prism sensor 20 is depicted. Single mode optical fiber 14 is bent through an angle of 2α, and the previously designated optical fiber 16 coupling the reflected radiant energy ray 48 from the prism sensor 20 to the spectrograph detector 24 is now simply a continuation of the single mode optic fiber 14. The sensor face 40 is ground and polished as with the first preferred configuration of FIG. 3; the face 40 is ground part way through the optical fiber core 30 and its normal is at an angle α with the incident radiant energy ray 44. This configuration eliminates the reflecting sensor face 42 and, advantageously, can be part of a string of refraction sensors, can be fabricated from a continuous single mode fiber from the radiant energy source to the detector, and has the potential to be done inexpensively.

Figure 8:
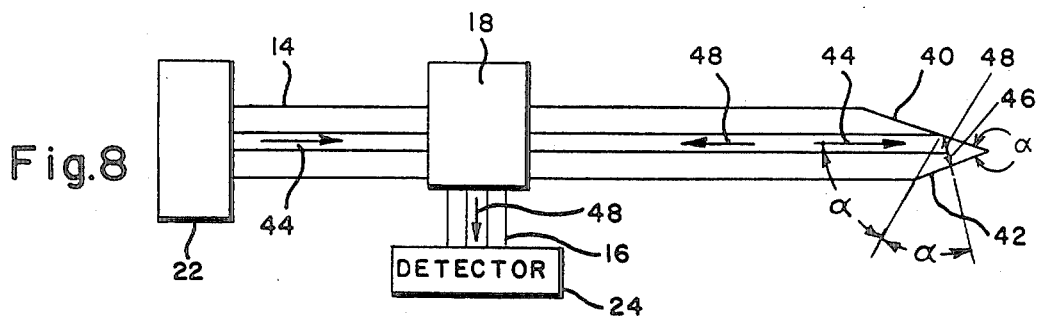
FIG. 8 is a schematic enlargement of a third preferred embodiment of the sensor tip region of the index of refraction instrument of FIG. 5.

Referring more particularly to FIG. 8, a third configuration of prism sensor 20 is depicted. The end of single mode optical fiber 14 itself becomes the prism sensor 20, and the detector return fiber 16 becomes identical with the light source supply fiber 14 up to the bidirectional coupler 18. The end of optical fiber 14 is ground and polished so that the normal of sensing face 40 makes an angle of α with the incident ray 44. The second reflecting face 42 is ground and polished so that it makes an angle of α with face 40. Face 42 is then mirrored so that ray 46 returns directly back along ray 46 and ray 44 in optical fiber core 30 until it meets the bidirectional coupler 18, which separates ray 48 from ray 44 and directs ray 48 to the spectograph detector 24. The proper alignments of faces 40 and 42 is done as before in the first preferred configuration of FIG. 3.

The advantage of the configuration of FIG. 8 is that the probe 12 is only the diameter of the single mode fiber 14 or about 75 microns. The active part of the sensing face 40 is the fiber core 30 which is about 5 microns in diameter.

Figure 9:
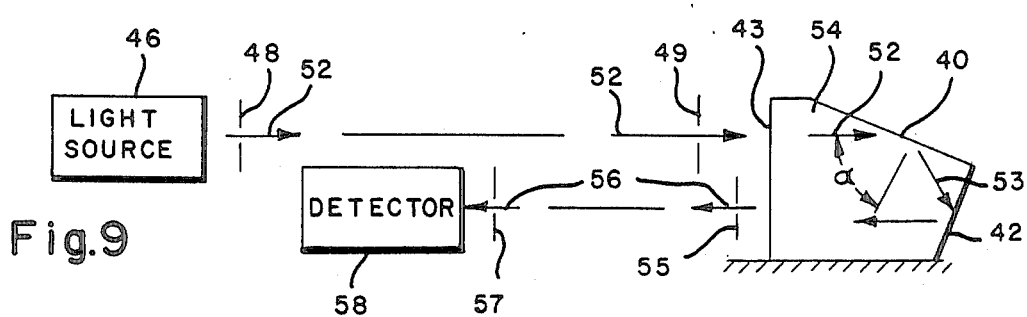
FIG. 9 is a schematic plan view of a second presently preferred embodiment of the index of refraction instrument of this invention.

Referring now more particularly to FIG. 9, a second preferred embodiment of the index of refraction instrument is shown generally at 50 and is designed as a more permanent and accurate installation suitable for laboratory use. Broad-band white light source 46 is optically coupled to prism 54 through collimating slits 48 and 49. The light ray 52 enters prism 54 through prism face 43 which has an antireflecting coating on it. Light ray 52 is then partially reflected from prism sensor face 40 depending upon the index of refraction of the fluid external to face 40. Light ray 53 is then totally reflected by mirrored prism face 42 and leaves prism 40 through prism face 43 as light ray 56. Light ray 56 is then collimated by slits 55 and 57 and enters the spectograph detector 58 where the band edge wavelength is measured as before by noting at what wavelengths the spectral intensity changes abruptly. The band edge wavelength is then continuously converted to an index of refraction of the unknown material. The wavelength range of the light source 46 is specifically chosen in conjunction with the prism material and prism sensor face angle α to cover the external index of refraction range of interest as before. The fabrication and alignment of prism sensor faces 40 and 42 is accomplished as before.

Because the embodiment of FIG. 9 is permanent, not expendable, and is a laboratory instrument not a remote one, a greater accuracy and measurement range of indices of refraction is possible. Light ray 52 can be more intense and, thus, highly collimated, as well as polarized. Light ray 56 will also be more highly collimated as a result of this and collimating slits 55 and 57, resulting in a spectrograph detector 58 with an accuracy of 0.1 nanometers and an accuracy of the index of refraction of approximately one part per million.

The prism sensors 20 of FIGS. 3, 7, and 8 and prism sensor 54 of FIG. 9 have dynamic ranges and sensitivities to the index of refraction of the external sample that are determined by the material from which they are made. With the prisms made out of silica or germanium doped silica, such as in optical fibers, and with a visible light source of 300 nanometers bandwidth, the approximate range for the index of refraction is 0.02 with a sensitivity of $1 \times 10^{-5}$. If the prism material is flint glass F2, the range is 0.05 in the index with a sensitivity of $2.5 \times 10^{-5}$. If dense flint glass SF-10 is used for the prism material, then the range for the index measurement is 0.08 with a sensitivity of $4 \times 10^{-5}$; whereas if titanium dioxide (Rutile) is used, the index range would be 0.5 with a sensitivity of $2 \times 10^{-4}$. The above sensitivities are for the remote expendable probe 12 and spectograph detector 24 of FIG. 5.

Importantly, the measurement of this refraction sensor is inherently stable because the desired index of refraction modulates the wavelength (color) rather than the intensity of the sensor signal. The refraction sensor can also be made extremely small to correspond to the diameter of the optical fiber transmitting means. Because of the presence of the optical fiber used to transmit the radiant energy signal from the prism sensor, the refraction sensor as configured in FIGS. 3, 5, 7, and 8 is capable of remote and continuous measurements, and can be made expendable, by simply unreeling the thin optical fiber 16 as the measurements are being made and severing it when the measurement is completely recorded by the spectograph detector 24. The sensor 20, optical fibers 14 and 16, and light source 22 are then left in-situ. The continuously reading detector is distant from the measurement spot and is retained, as for instance on board a ship when ocean measurement are made. Finally, the refraction sensor when configured for laboratory use, as in FIG. 9, is capable of extreme accuracy.

The invention may be embodied in other specific forms without departing from its spirit or essential characteristics. The described embodiments are to be considered in all respects only as illustrative and not restrictive, and the scope of the invention is, therefore, indicated by the appended claims rather than by the foregoing description. All changes which come within the meaning and range of equivalency of the claims are to be embraced within their scope.

What is claimed and desired to be secured by a U.S. Letters Patent is:

1. An index of refraction sensor for monitoring the index of refraction of a material external to a sensing face on the sensor by establishing at least one critical wavelength comprising in combination:
   a first radiant energy path means comprising a single mode optical fiber waveguide and a second radiant energy path means comprising an optical fiber waveguide, said second optical fiber waveguide capable of being long enough to allow remote detection of the index of refraction;

a broad-band radiant energy source means optically coupled to said first radiant energy path means, having a band width chosen to span any of said critical wavelengths expected in a given application;

collimating means the radiant energy path to render the incident radiant energy a parallel beam;

sensing means prismatically configured so as to provide a direct reflective path from said first waveguide means, through said sensing means, to said second waveguide means, said sensing means possessing a sensing face which reflects a portion of the broadband incident radiant energy as a function of the index of refraction of the material external to the prism sensor face, the portion including any of said expected critical wavelengths;

detecting and monitoring means optically coupled to said second radiant energy path means for simultaneously and continuously detecting the intensities of the separate wavelengths of the broad-band radiant energy that is reflected from the prism sensor face to the detector, the detecting means continuously correlating said at least one wavelengths where the reflected spectral intensity abruptly changes with the index of refraction of the material external to the sensing means.

2. The refraction sensor defined in claim 1 wherein the radiation source is operable to emit radiant energy in the visible and/or infrared region of the electromagnetic spectrum.

3. The refraction sensor defined in claim 1 wherein the first radiant energy path means comprises two collimating slits and the second radiant energy path means is also comprised of two collimating slits to couple the radiant energy source means in a parallel manner to the sensing means, and the sensing means to the detecting means, respectively.

4. The index of refraction sensor defined in claim 1 wherein the sensing means comprises a prism and prism face that reflects incident radiation in a band between certain wavelengths, including at least one critical wavelengths any such wavelengths being functions of the index of refraction of the fluid external to the prism face.

5. The index of refraction sensor defined in claim 1 wherein the sensing means is fabricated from a transparent material whose index of refraction is a different function of wavelength than that of the material external to the sensing means, such that the ratio of the external index to that of the sensor is variable and less than one.

6. The index of refraction sensor defined in claim 5 where the sensing means is fabricated from silica ($SiO_2$) or germanium doped Silica ($GeO_2$:$SiO_2$) for use in seawater.

7. The index of refraction sensor defined in claim 1 wherein the first and second radiant energy path means are the identical clad single mode optical fiber with a core and the sensing means is fabricated directly on the end of the core of the fiber and includes a second nonsensing face that is mirrored and returns the incident radiant energy from the sensing face back along the identical single mode optical fiber path that transmitted the original radiant energy.

8. The index of refraction sensor defined in claim 1 wherein the first and second radiant energy path means are embodied in one, continuous clad single mode fiber and the sensing means is fabricated with a single face that is ground partially into the optical fiber core, and the reflected radiant energy from said sensing face is coupled directly into the second optical path means to the detector.

9. A method for sensing the index of refraction in the oceans at locations that are remote from a detector having prism sensing means, light source, and optical fiber which are expendable, the method comprising:

fabricating an index of refraction sensor from a transparent material having a sensing face with spectral reflection characteristics over a preselected bandwidth which includes at least one expected critical wavelength as a function of the index of refraction of the external fluid, said sensor being prismatically configured so as to provide a second mirrored face to reflect the reflected radiant energy through said sensing means;

providing a broad-band radiation source for said preselected bandwidth;

optically coupling the sensor to the radiation source with a single mode optical fiber waveguide;

providing a detector capable of simultaneously and continuously detecting the intensity change of all the individual wavelengths reflected from the prism sensing face as a function of the index of refraction of the external fluid;

optically coupling the sensing means to the detector with an extended, reeled second optical fiber waveguide;

unreeling the extended second optical waveguide as the measurement is made;

continuously sensing the index of refraction by directing the radiation along a direct reflective path from said first optical fiber waveguide, through said prism sensing means, to said second optical fiber waveguide, and continuously detecting the spectral intensities of the radiation reflected from the sensing means as a function of the index of refraction external to the sensing means; and allowing said second optical fiber waveguide to be severed when the measurement is complete.

10. A sensor as recited in claim 1 wherein the detecting and monitoring means include a multi-pixel detector configured for simultaneous imaging of the spectral intensities of the reflected radiant energy.

11. A sensor as recited in claim 10 wherein the multi-pixel detector is a charge-coupled device.

* * * * *